United States Patent [19]
Nakayama et al.

[11] 4,087,442
[45] May 2, 1978

[54] PROCESS FOR PRODUCING INDOLINE

[75] Inventors: Yoshiki Nakayama, Shimizu; Hironobu Sano, Fuji; Sataro Okamura; Kazunari Hirao, both of Ihara, all of Japan

[73] Assignee: Ihara Chemical Industry Co., Ltd., Tokyo, Japan

[21] Appl. No.: 736,340

[22] Filed: Oct. 28, 1976

[30] Foreign Application Priority Data

Aug. 18, 1976  Japan .................................. 51-98325

[51] Int. Cl.$^2$ .......................................... C07D 209/04
[52] U.S. Cl. ........................ 260/326.11 R; 260/319.1
[58] Field of Search ............................... 260/326.11 R

[56] References Cited
PUBLICATIONS

Remers, et al., Chem. of Heterocyclic Cmpds.–Indole Part I, pp. 463–467, Wiley–Interscience, 1972.
Chem. Abstracts, 23:2715.

Primary Examiner—Ethel G. Love
Attorney, Agent, or Firm—Oblon, Fisher, Spivak, McClelland & Maier

[57] ABSTRACT

Indoline is produced by a cyclization of o-halogenophenethylamine compound having the formula

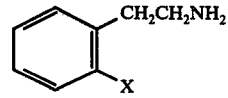

wherein X represents a halogen atom in the presence of a copper type catalyst and ammonia.

5 Claims, No Drawings

PROCESS FOR PRODUCING INDOLINE

BACKGROUND OF THE INVENTION

The present invention relates to a process for producing indoline. Indoline

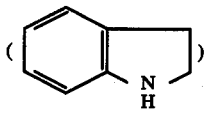

is used as an intermmediate of indole

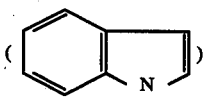

which is a starting material for producing agricultural chemicals, medicines, dyes and others, or an intermediate of indoline derivatives.

It has been known to produce indoline by reducing o-nitrophenethyl alcohol with zinc and calcium chloride to produce o-aminophenethyl alcohol and performing a cyclization in the presence of hydrochloric acid as follows.

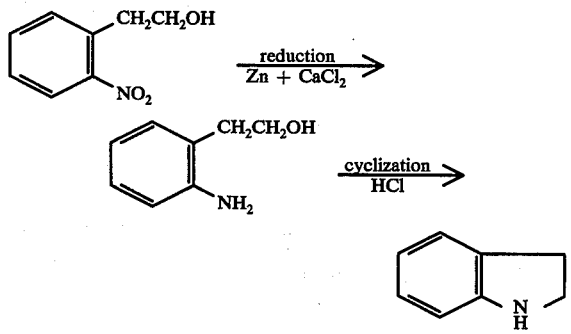

However, in the method, phenethyl alcohols are easily decomposed by heating and by-products of polymers are formed in the reaction and the deterioration of the catalyst is remarkable, disadvantegeously, whereby, it has been difficult to obtain indoline having high purity in high yield.

SUMMARY OF THE INVENTION

Accordingly, it is an object of the present invention to overcome the disadvantages and to produce indoline having high purity in high yield.

The object of the invention has been attained by producing indoline by a cyclization of o-halogenophenethylamine compound having the formula

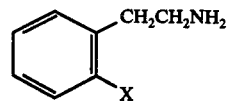

wherein X represents a halogen atom, in the presence of a copper type catalyst and ammonia.

DETAILED DESCRIPTION OF THE PREFERRED EMBODIMENTS

The reaction of the invention is as follows.

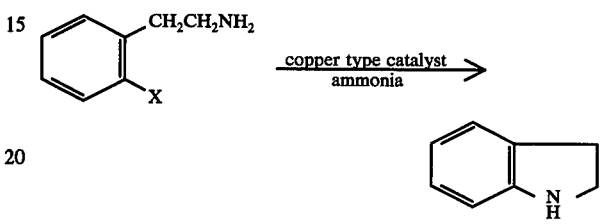

The halogen atoms of o-halogenophenethylamines can be chlorine, bromine, fluorine or iodine atom. In the practical operation, it is preferable to use o-chlorophenethylamine and o-bromophenethylamine.

The catalysts used in the invention can be copper type catalysts to feed copper ions in the reaction system. Suitable catalysts include methallic copper and inorganic copper compounds and copper salts of organic acids, such as cuprous chloride, cupric chloride, cuprous bromide, cupric bromide, cuprous iodide, cupric iodide, cuprous oxide, cupric oxide, cuprous hydroxide, cupric hydroxide, cuprous cyanide, cupric cyanide, cuprous nitrate, cupric nitrate, cuprous sulfate, cupric sulfate, cuprous oxalate, cupric oxalate, cuprous acetate, cupric acetate ect..

An amount of the catalyst is usually 0.1 to 20 wt. % preferably 1 to 5 wt. % as Cu to the starting material.

The reaction of the invention is carried out in the presence of ammonia, such as liquid ammonia, ammonia aqueous solution or ammonia-alcohol solution. An amount of ammonia is 2 to 20 moles preferably 3 to 10 moles per 1 mole of the starting material.

The reaction is usually carried out at lower than 200° C preferably 100° to 150° C for about 1 to 4 hours under high pressure for maintaining ammonia since the dealkylation and the formation of by-products of polymers are caused at high reaction temperature.

The reactions were carried out by using o-chlorophenethylamine (OCPA) under varying the type of the catalyst, the amount of the catalyst, the amount of ammonia water, the reaction temperature and the time. The resulting reaction products were analyzed according to the gas chromatography. The results are shown in the following table.

| No. | Catalyst | Conditions of reaction | | | | Composition (%) | | | Yield of indoline (%) |
|---|---|---|---|---|---|---|---|---|---|
| | | | Ammonia water | Temp. | Time | OCPA | Indole | Indoline | |
| 1 | CuCl | 3wt % | NH$_4$OH20% | 100° C | 2$^{hr}$ | 9.5 | 0.3 | 88.7 | 80.7 |
| 2 | " | " | " | 150 | " | 0.4 | 3.0 | 95.0 | 90.2 |
| 3 | " | 1wt % | " | " | " | 3.7 | 2.0 | 92.5 | 84.2 |
| 4 | " | 3wt % | " | " | 1.5 | 0.6 | 2.8 | 94.6 | 89.4 |
| 5 | " | " | NH$_4$OH15% | " | 2 | 0.4 | 3.1 | 95.2 | 90.5 |
| 6 | " | " | " | " | 1.5 | 0.7 | 2.8 | 94.8 | 90.3 |
| 7 | CuCl$_2$ | " | " | " | 2 | 4.6 | 2.0 | 90.5 | 81.9 |
| 8 | CuO | " | " | " | " | 10.8 | 0.1 | 86.9 | 78.0 |

-continued

| No. | Catalyst | Conditions of reaction | | | Composition (%) | | | Yield of indoline (%) |
|---|---|---|---|---|---|---|---|---|
| | | Ammonia water | Temp. | Time | OCPA | Indole | Indoline | |
| 9 | Cu | " | " | " | 9.2 | 3.5 | 85.0 | 75.6 |
| 10 | Cu(OH)$_2$ | " | " | 3 | 7.0 | 1.7 | 87.8 | 80.0 |
| 11 | Cu(NO$_3$)$_2$ | " | " | " | 7.7 | 1.1 | 86.9 | 78.2 |
| 12 | CuC$_2$O$_4$ | " | " | " | 9.0 | 0.5 | 86.0 | 77.5 |
| Ref. | — | NH$_4$OH20% | 200 | 6 | 98.2 | 0 | 0 | 0 | note: CuC$_2$O$_4$ : cupric oxalate

As it is clear from the table, in accordance with the process of the invention, indoline having high purity can be obtained in high yield.

In the process of the invention, the cyclization of o-halogenophenethylamines is carried out in the presence of the copper type catalyst and ammonia. Accordingly, there is no formation of a by-product as the conventional process and even though the amount of the unreacted starting material is large, the unreacted starting material can be recovered and reused as the starting material. Moreover, the product of indole having high purity can be easily produced in high yield.

The invention will be illustrated by certain examples.

EXAMPLE 1

In an autoclave, 157 g of o-chlorophenethylamine (purity of 99.0%), 4.7 g of cuprous chloride as a catalyst (3% as CuCl to the starting material) and 375 g of ammonia water (67.5% as NH$_4$OH to the starting material), were charged and the reaction of the mixture was carried out at 150° C for 4 hours. After the reaction, the reaction mixture was analyzed according to the gas chromatography.

The composition of the reaction mixture had the following components

| o-chlorophenethylamine | 0.1 wt. % |
|---|---|
| indole | 3.3 wt. % |
| indoline | 95.3 wt. % |

The reaction mixture was distilled to obtain 106 g of pure indoline. The yield was 89.1% to the stoichiometrical amount.

EXAMPLE 2

In accordance with the process of Example 1 except using o-bromophenethylamine as the starting material, the cyclization was carried out. As the result, the compostion had the following components.

| o-bromophenethylamine | 0.1 wt. % |
|---|---|
| indole | 3.2 wt. % |
| indoline | 95.5 wt. % |

The yield of indoline after the distillation was 89.7%.

EXAMPLE 3

In accordance with the process of Example 1 except using cupric oxalate as the catalyst, the cyclization was carried out. As the result, the composition had the following components.

| o-chlorophenethylamine | 4.7 wt. % |
|---|---|
| indole | 2.0 wt. % |
| indoline | 89.0 wt. % |

The yield of indoline after the distillation was 80.1%.

What is claimed is:

1. A process for producing indoline which comprises cyclization of an o-halogenophenethylamine having the formula

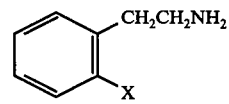

wherein X represents a halogen atom, in the presence of ammonia, and a copper type catalyst which supplies copper ions; and wherein said cyclization is carried out at a temperature below 200° C, under pressure sufficient to retain said ammonia.

2. The process according to claim 1 wherein said o-halogenophenethylamine is chloro-, bromo-, fluoro- or iodo-phenethylamine.

3. The process according to claim 1 wherein said o-halogenephenethylamine is chlorophenethylamine or bromophenethylamine.

4. The process according to claim 1 wherein said catalyst is combined at a ratio of 0.1 to 20 wt. % as Cu to o-halogenephenethylamine.

5. The process according to claim 1 wherein said ammonia is liquid ammonia, ammonia aqueous solution or ammonia alcohol solution and said ammonia is combined at a ratio of 2 to 20 moles per 1 mole of o-halogenephenethylamine.

* * * * *